United States Patent

Swaile

[11] Patent Number: 6,149,897
[45] Date of Patent: Nov. 21, 2000

[54] PROCESS FOR MAKING ANHYDROUS COMPOSITIONS CONTAINING SOLUBILIZED, ENHANCED ANTIPERSPIRANT ACTIVE

[75] Inventor: David Frederick Swaile, Cincinnati, Ohio

[73] Assignee: The Procter & Gamble Company, Cincinnati, Ohio

[21] Appl. No.: 09/379,991

[22] Filed: Aug. 24, 1999

[51] Int. Cl.$^7$ ............... A61K 7/32; A61K 7/34; A61K 7/38; A61K 7/00
[52] U.S. Cl. ............... 424/65; 424/66; 424/68; 424/400; 424/401
[58] Field of Search ............... 424/65, 66, 68, 424/400, 401

[56] References Cited

U.S. PATENT DOCUMENTS

| | | | |
|---|---|---|---|
| 3,420,932 | 1/1969 | Jones et al. | 424/47 |
| 3,904,741 | 9/1975 | Jones et al. | 423/462 |
| 3,928,545 | 12/1975 | Jones et al. | 423/463 |
| 4,435,382 | 3/1984 | Shin et al. | 424/66 |
| 4,704,271 | 11/1987 | Hourihan et al. | 424/66 |
| 4,719,102 | 1/1988 | Randhawa et al. | 424/66 |
| 4,720,381 | 1/1988 | Schamper et al. | 424/66 |
| 4,767,875 | 8/1988 | Vincenti et al. | 556/175 |
| 4,781,917 | 11/1988 | Luebbe et al. | 424/65 |
| 5,179,220 | 1/1993 | Katsoulis et al. | 556/27 |
| 5,486,347 | 1/1996 | Callaghan et al. | 423/623 |
| 5,643,558 | 7/1997 | Provancal et al. | 424/66 |

FOREIGN PATENT DOCUMENTS

| | | |
|---|---|---|
| 0 007 191 A1 | 1/1980 | European Pat. Off. . |
| 0 183 171 A2 | 6/1986 | European Pat. Off. . |
| 0 191 628 A2 | 8/1986 | European Pat. Off. . |
| 2 048 229 | 12/1980 | United Kingdom . |
| WO 96/33800 | 10/1996 | WIPO . |
| WO 97/34577 | 9/1997 | WIPO . |
| WO 98/58626 | 12/1998 | WIPO . |

*Primary Examiner*—Shelly A. Dodson
*Attorney, Agent, or Firm*—William J. Winter

[57] ABSTRACT

Disclosed is a process for making anhydrous compositions containing solubilized, enhanced antiperspirant active, which process comprises the steps of (A) heating an aqueous solution comprising from about 24% to about 55% by weight of a solubilized, non-enhanced, aluminum-containing antiperspirant active at a temperature of from 120° C. to about 200° C. for a period of time of from about 1 minute to about 15 minutes to form a solubilized, enhanced, aluminum-containing antiperspirant active; (B) adding an anhydrous solvent to the aluminum-containing solution at a weight ratio of the anhydrous solvent to the aluminum-containing antiperspirant actives of from about 1:2 to about 20:1; and C removing water from the anhydrous solvent-containing solution to form an anhydrous composition containing solubilized, enhanced, aluminum-containing, antiperspirant active. The process provides an improved method for making antiperspirant compositions containing solubilized, enhanced antiperspirant active.

22 Claims, 1 Drawing Sheet

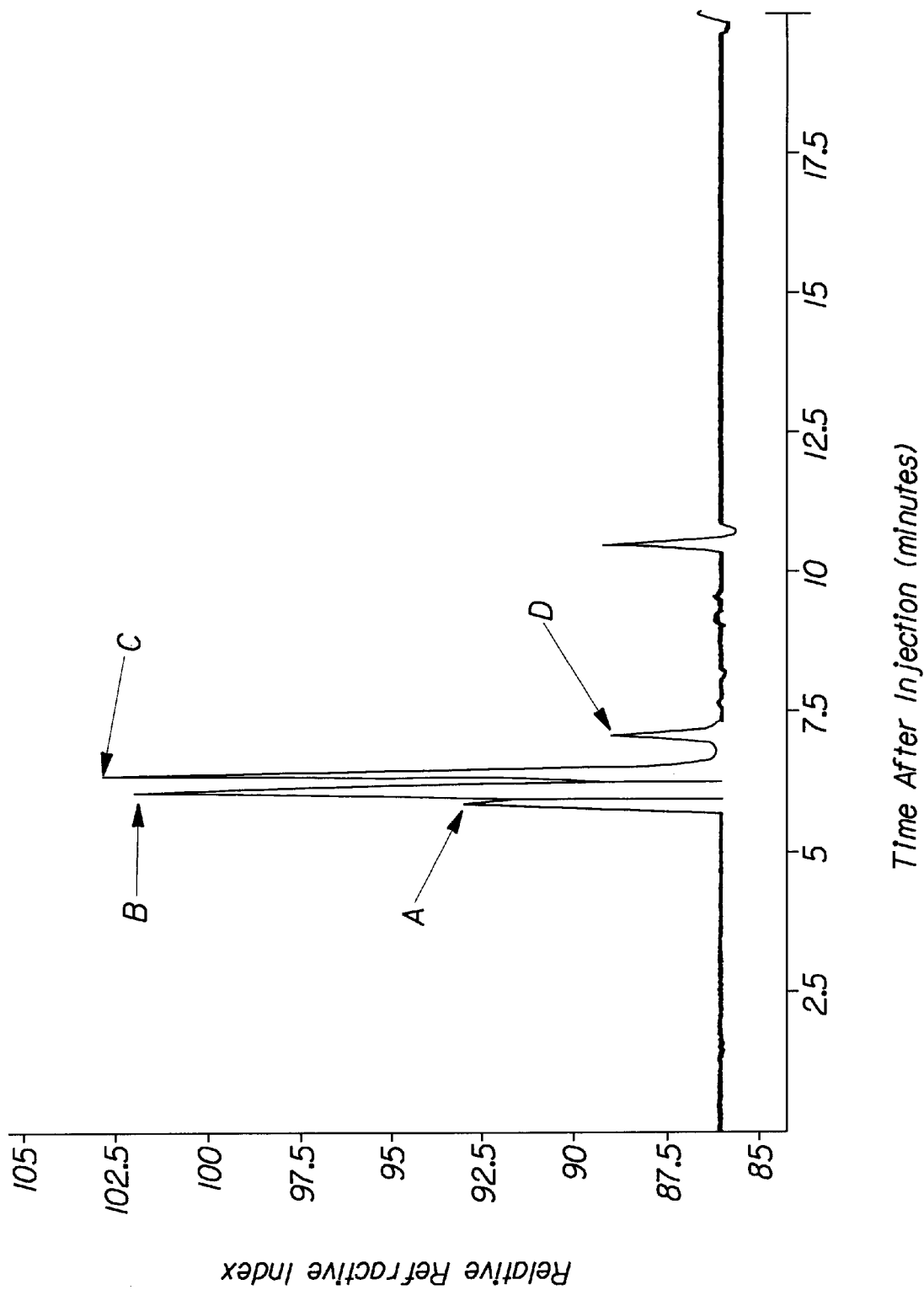

PROCESS FOR MAKING ANHYDROUS COMPOSITIONS CONTAINING SOLUBILIZED, ENHANCED ANTIPERSPIRANT ACTIVE

FIELD OF INVENTION

This invention relates to a process for making anhydrous compositions comprising solubilized, enhanced antiperspirant active. The process provides improved manufacturing efficiency, including the application of fewer intermediate manufacturing steps in making a stable, anhydrous composition containing solubilized enhanced antiperspirant actives.

BACKGROUND OF THE INVENTION

Most topical antiperspirant products available today contain antiperspirant actives such as zirconium and aluminum salts, most typically in their enhanced form (e.g., improved or activated antiperspirant active). These enhanced aluminum and zirconium salts are formulated into topical products as either suspended particulate solids or as solubilized or partially solubilized active in an aqueous or alcoholic solvent.

Solubilized, enhanced antiperspirant active can provide a topical product with improved low residue performance and antiperspirant efficacy. These solubilized actives can be formulated into an anhydrous solvent to provide improved dry feel application, antiperspirant efficacy and stability of the dissolved active. Examples of anhydrous solvents commonly used or otherwise known for use in solubilizing these antiperspirant actives include ethylene glycol, diethylene glycol, butylene glycol, 1,2-proplyene glycol, 1,3-propylene glycol, 1,3-butylene glycol (1,3-butane-diol), glycerine (1,2,3-trihydroxy propane), 2-methyl-2,4-pentane-diol (hexylene glycol), 1,2-hexanediol, 2-ethyl-1,3-hexane-diol, 1,2,6-hexanetriol, ethanol, tripropylene glycol, propylene glycol methyl ether, dipropylene glycol methyl ether, and so forth.

Anhydrous compositions containing solubilized, enhanced, antiperspirant active are formulated by any of a variety of known methods. Most of these methods include an initial or intermediate manufacturing step in which aluminum or aluminum-zirconium salts are activated to form improved or enhanced-efficacy antiperspirant active. These activation steps typically involve the application of heat to an aqueous active solution to produce the desired enhanced antiperspirant, followed by the rapid evaporation or removal of water from the heated solution to thus stabilize the enhanced antiperspirant in its improved or enhanced form. The improved or enhanced active contains a higher concentration of lower molecular weight aluminum or aluminum-zirconium polymers making up the active salt. It is believed that the lower molecular weight active polymers provide improved antiperspirant efficacy.

Many variations of the above described method are known for making anhydrous compositions containing solubilized, enhanced, antiperspirant active. One such variation involves the dissolution of enhanced antiperspirant active powder or solids in an aqueous solution containing an anhydrous solvent, followed by the rapid evaporation of water from the enhanced active solution. As with the above-described process, it is important to quickly evaporate the water after dissolution to prevent or minimize the polymeric shift of the enhanced antiperspirant active to a larger, less effective, molecular weight species. It is believed that any such polymeric shift will result in a loss of antiperspirant efficacy.

These methods for making anhydrous compositions containing dissolved enhanced active, however, typically involve a long series of relatively inefficient or costly process steps. For example, many of the prior art methods require an initial series of steps resulting in the formation of spray dried enhanced antiperspirant powder, which is then redissolved in an aqueous solution to begin the next manufacturing sequence. Other methods have avoided this wasteful spray drying-redissolution sequence by making the enhanced antiperspirant active initially in a dilute aqueous solution containing not more than 20% by weight of aluminum active, heating the dilute solution to a temperature of up to 105° C. for several hours to form an enhanced aluminum-containing active, adding an anhydrous solvent, and then rapidly evaporating the water from the solution to form the desired anhydrous composition containing the enhanced aluminum active and the added anhydrous solvent. Although this process avoids the spray drying-redissolution step described above, it requires the use of relative dilute active solutions (not more than 20% by weight of the solution) which then requires substantial amounts of energy during the evaporation sequence to rapidly remove such large amounts of water.

It is therefore an object of the present invention to provide an improved process for making anhydrous compositions containing solubilized, enhanced, antiperspirant actives, wherein the improved process involves a more efficient manufacturing sequence that reduces manufacturing costs, simplifies the manufacturing sequence, and reduces production times.

SUMMARY OF THE INVENTION

The present invention is directed to a process for making anhydrous compositions containing solubilized, enhanced antiperspirant active. The process comprises the steps of (A) heating an aqueous solution comprising from about 24% to about 55% by weight of a solubilized, non-enhanced, aluminum-containing antiperspirant active at a temperature of from 120° C. to about 200° C. for a period of time of from about 1 minute to about 15 minutes to form a solubilized, enhanced, aluminum-containing antiperspirant active; (B) adding a zirconium-containing antiperspirant active to the heated solution to provide the solution with a range of from about 24% to about 60% by weight of the combined solubilized zirconium-containing and aluminum-containing antiperspirant actives; (C) adding an anhydrous solvent to the zirconium and aluminum-containing solution at a weight ratio of the anhydrous solvent to the combined zirconium and aluminum-containing antiperspirant actives of from about 1:2 to about 20:1; (D) removing water from the anhydrous solvent-containing solution to form an anhydrous composition containing solubilized, enhanced, zirconium-containing and aluminum-containing, antiperspirant active.

It has been found that the process of the present invention provides improved efficiency in making antiperspirant compositions containing solubilized, enhanced, antiperspirant active. The process is especially useful in that it involves the use of fewer intermediate manufacturing steps than other known methods for making stable antiperspirant active solutions, and/or can help reduce manufacturing costs and production times.

BRIEF DESCRIPTION OF THE DRAWING

FIG. 1 is an example of chromatogram for an enhanced zirconium-aluminum salt. The chromatogram is generated in accordance with the gel permeation chromatography (GPC)

methodology described herein. This methodology is used to help define "enhanced antiperspirant active" for purposes of characterizing the type of antiperspirant active made in accordance with the process of the present invention. The vertical axis represents relative refractive indices. The horizontal axis represents the duration of time (minutes) required for the different polymer species of a zirconium-aluminum salt to pass through the GPC column. Peaks I–II are represented as a single spike at about 5.84 minutes (A); Peaks III, IV and V are represented at about 6.09 minutes (B), 6.39 minutes (C) and 7.08 minutes (D), respectively. Peaks I–II correspond to co-eluting aluminum and zirconium polymer species; Peaks III, IV and V correspond to other aluminum polymer species in the injected sample. The unidentified peak at the far right of the chromatogram is a halogen peak associated with the salt sample.

DETAILED DESCRIPTION

The process of the present invention, including the essential limitations and optional characteristics, are described in detail hereinafter. All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The term "anhydrous" as used herein, unless otherwise specified, means that the referenced material or composition contains less than 20%, preferably less than 10%, more preferably less than 5%, most preferably zero percent, by weight of water.

The term "enhanced antiperspirant" as used herein, unless otherwise specified, means an aluminum-containing antiperspirant material wherein molecular weight distribution of the aluminum-containing material, which is in polymeric form, is measurably shifted to lower molecular weight polymers relative to the polymer distribution. In this context, the measurable shift is determined in accordance with the GPC methodology defined herein.

The process of the present invention can comprise, consist of, or consist essentially of the essential elements and limitations of the invention described herein, as well as any of additional or optional ingredients, components, or limitations described herein.

Process

The process of the present invention provides a more efficient method for making anhydrous compositions comprising solubilized antiperspirant active. The process described herein may be a continuous or batch process, preferably a continuous process. The anhydrous compositions made in accordance with the process can be used as raw materials or manufacturing intermediates to formulate a variety of anhydrous antiperspirant and deodorant products.

The first step of the process of the present invention is an initial heating step, wherein the initial heating step comprises heating an aqueous solution comprising from about 24% to about 55%, preferably from about 30% to about 50%, more preferably from about 30% to about 40%, by weight of a solubilized aluminum-containing material at a temperature of from about 120° C. to about 200° C., preferably from about 140° C. to about 190° C., more preferably from about 140° C. to about 180° C., for a period of time ranging from about 1 minute to about 15 minutes, preferably from about 1 minute to about 5 minutes, more preferably from about 1 minute to about 3 minutes.

The initial heating will typically take place in a closed heat exchanger system such as a recycling loop heat exchanger. Heating times will vary within the above-recited ranges depending on a variety of factors, including the type of heat exchanger equipment used. The recycling loop heat exchanger, for example, generally requires longer heating times than other closed heat exchanger systems.

In accordance with the initial heating step, the aqueous solution containing the aluminum active can be prepared by any known or otherwise effective means for preparing an active solution containing aluminum or aluminum and zirconium salts. These aqueous solutions may comprise other solvents other than water, but most typically will comprise water as the primary or only liquid solvent at this particular point in the process.

A second but optional step of the process of the present invention is an initial mixing step, wherein the initial mixing step comprises adding a zirconium-containing material to the heated aqueous solution to provide the solution with a range of from about 24% to about 60%, preferably from about 30% to about 50%, more preferably from about 30% to about 40%, by weight of the combined solubilized zirconium-containing and aluminum-containing materials. The zirconium-containing material can be added prior to, during or after the initial heating step, but is preferably added at after the initial heating step. The atomic ratio of aluminum to zirconium in the aqueous solution is preferably from about 10:1 to about 1:10, more preferably from about 6:1 to about 1:6, even more preferably from about 3:1 to about 1:6.

A third step of the process of the present invention comprises an anhydrous solvent mixing step, wherein the anhydrous solvent mixing step comprises adding an anhydrous solvent to the zirconium and aluminum-containing solution at a weight ratio of the anhydrous solvent to the combined zirconium and aluminum-containing materials of from about 1:2 to about 20:1, preferably from about 1:1 to about 10:1, more preferably from about 2:1 to about 4:1. The pH of the aluminum or aluminum and zirconium-containing solutions throughout the process of the present invention, including the anhydrous solvent mixing step, should be maintained within a pH range of from about 2 to about 5.

Neutral amino acids such as glycine can be added at any suitable point in the process to provide an amino acid complex with aluminum or aluminum and zirconium containing-materials. The neutral amino acid is preferably added to provide an aluminum (or aluminum and zirconium) to neutral amino acid weight ratio of from about 0.25:1 to about 5:1, more preferably from about 0.5:1 to about 2:1.

Anhydrous solvents suitable for use in the anhydrous solvent mixing step include any anhydrous solvent known in the formulations arts that when added to the heated solution, alone or in combination with other anhydrous solvents, results in or allows for the continued dissolution of the aluminum or aluminum and zirconium-containing materials in the heated solution after water removal. Non limiting examples of suitable anhydrous solvents include ethylene glycol, polyethylene glycols, dipropylene glycol, sorbitol, diethylene glycol, butylene glycol, hexylene glycol, 1,2-proplyene glycol, 1,3-propylene glycol, glycerine, 1,2-hexanediol, 2-ethyl-1,3-hexane-diol, 1,2,6-hexanetriol, ethanol, phthalate co-solvents, tripropylene glycol, propylene glycol methyl ether, isopropyl glyerol ether, dipropylene glycol methyl ether and combinations thereof. Preferred are propylene glycol, glycerin, butylene glycol, diethylene glycol, dipropylene glycol, 1,2-hexandiol, isopropyl glycerol ether, and combinations thereof. Other suitable non aqueous solvents include those polar solvents described in U.S. Pat. No. 5,429,816, which descriptions are incorporated herein by reference.

A fourth step of the process of the present invention comprises a water removal step, wherein water is removed from the anhydrous solvent-containing solution to form an anhydrous liquid composition containing solubilized zirconium-containing material and solubilized aluminum-containing material. The anhydrous composition can then be used as a raw material or manufacturing intermediate for use in making a variety of topical antiperspirant and deodorant products. Water removal can be accomplished by any known or otherwise effective means for removing water from an antiperspirant composition comprising solubilized aluminum-containing salts.

Preferred water removal means according to the fourth process step includes a variety of relatively rapid evaporation methods, including vacuum evaporation (e.g., under 150 mm Hg) at processing temperatures typically less than 150° C., more typically at a temperature of from about 20° C. to about 100° C. Vacuum evaporation may take place in any suitable vacuum evaporation system including rotary vacuum evaporators or flash vacuum evaporators, e.g., thin film evaporators. The evaporation process is preferably continuous, and evaporation times minimized to an average residence time within the evaporator of preferably less than about 3.5 hours, although such evaporation times will vary greatly with the type of evaporator equipment used, the volume of solution within the evaporator at any given time, the amount of water to be removed per volume of solution, and so forth. Other suitable water removal means are described in U.S. Pat. No. 5,643,558 (Provancal et al.); U.S. Pat. No. 4,781,917 (Luebbe et al.); and European Patent Application 0 404 533 A1 (Smith et al.), which descriptions are incorporated herein by reference.

The aluminum-containing material for use in the process of the present invention includes any inorganic or organic aluminum salt, preferably an aluminum halide, aluminum chlorohydrate, aluminum hydroxyhalides, zirconyl oxyhalides, zirconyl hydroxyhalides, or mixtures thereof. Suitable aluminum salts for use in this manner include those aluminum salts which conform to the formula:

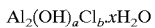

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Optional zirconium-containing materials for use in the process of the present invention include those which conform to the formula:

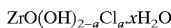

$$ZrO(OH)_{2-a}Cl_a \cdot xH_2O$$

wherein a is any number having a value of from about 0 to about 2; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

The various solutions used in the process of the present invention may further comprise other additional ingredients suitable for use as manufacturing aids, or which are otherwise known or effective for use in topical antiperspirant and deodorant products, provided that such other additional ingredients are compatible with the ingredients of the corresponding solution, or which do not unduly impair the process of the present invention and the intended benefits arising therefrom.

Non limiting examples of optional ingredients for use in the process include pH buffering agents; cosolvents or additional emollients; humectants; soothing agents; solid antiperspirant active; dyes and pigments; suspending or thickening agents; residue masking agents; wash-off aids; antimicrobial agents; chelants; perfumes; medicaments or other topical active material; preservatives; and so forth. Other non limiting examples of optional ingredients include those described in U.S. Pat. No. 4,049,792 (Elsnau); U.S. Pat. No. 5,019,375 (Tanner et al.); U.S. Pat. No. 5,429,816 (Hofrichter et al.); which descriptions are incorporated herein by reference.

II. Methodology

The term "enhanced antiperspirant active" is used interchangeably herein with the terms "activated antiperspirant active" or "improved antiperspirant" active. The enhanced antiperspirant as contemplated herein means any aluminum-containing antiperspirant material wherein the molecular weight distribution of the aluminum-containing material, which is in polymeric form, is measurably shifted to lower molecular weight polymers relative to the polymer distribution. The measurable shift is determined in accordance with the Gel Permeation Chromatography (GPC) methodology described hereinafter.

Anhydrous compositions containing solubilized, enhanced, antiperspirant active made in accordance with the process of the present invention are dissolved in 0.01M nitric acid to make a 1% solution of active and chromatographed using 5 μl injections in a series of three consecutive Waters μ Porasil Columns, 3.9×300 mm, 10 μm packing. Chromatograms are visualized using a Waters 410 Differential Refractometer. Samples are prepared immediately prior to analysis to prevent degradation. Relative peak areas and area ratios are calculated using a Waters Millennium Data System (Version 2.10 or equivalent).

The peaks observed in the chromatogram are designated in order of appearance on the chromatogram as Peaks I–II (appears as a single peak) and Peaks III, IV and V (see FIG. 1). The area of Peaks III, IV and V correspond to the relative concentration of aluminum polymer species exiting the column during the specified time period from the injected sample. The area of Peaks I–II correspond to the relative concentration of co-eluting aluminum and zirconium polymer species appearing initially on the chromatogram.

Prior to any analysis, the columns should be conditioned individually by repeated 100 μl injections of a 10% zirconium-aluminum trichlorohydrate glycine solution (containing at least 10% zirconium on a solid basis). Conditioning is complete when the area percent of Peaks I–II become relatively constant. During the conditioning process, the area percent of Peaks I–II will increase, and there will be reduction in retention for all peaks. Columns should be discarded when Peaks I and II are no longer resolved from Peak III.

Measurable shifts in the concentration of molecular weight polymer species to establish an enhanced antiperspirant active is then noted by an increase in the Peak III to Peak IV area ratios as compared to the same active as measured prior to activation. The activate antiperspirant active made in accordance with the process of the present invention preferably has a Peak IV to Peak III area ratio of at least about 0.1:1, more preferably at least about 0.3:1.

EXAMPLES

The following Example illustrates a specific embodiment of the process of the present invention, but is not intended to be limiting thereof. Other modifications can be undertaken by the skilled artisan without departing from the spirit and scope of this invention.

A 30% solution (active basis) of conventional aluminum chlorhydrate (metal to chlorine ratio of 2.0) is heated to 175° C. for 3 minutes to provide an enhanced aluminum chorohydrate solution. The enhanced active solution is mixed in a continuous flow at a 1:1 weight ratio with a 30% solution (active basis) of zirconium hydroxychloride glycinate (Zr:Cl mole ratio of 1:1, Zr:Gly mole ratio of 1:1) resulting in a 30% solution (active basis) of enhanced aluminum zirconium trichlorohydrate gly (AlZr mole ratio of 3.11, metal to chlorine mole ratio of 1.58). The enhanced aluminum zirconium is mixed in a continuous flow at a 1:0.6 weight ratio with 1,2-hexanediol. The mixture is then fed at about 3–4 gallons/hour into a type JHE flash evaporator (APV Crepacao Inc., Tonawanda, N.Y., evaporator modified by mounting to the top of the flash chamber a 3 foot rectification tower filled with about 2.5 feet of 0.5 inch ceramic Berl saddles) maintained at about 60 mm Hg (absolute pressure) from which is drawn about 1 gallon/hour of a clear solution comprising 62% 1,2-hexanediol, about 33% by weight of enhanced aluminum zirconium trichlorhydrate gly (measureable shift in the Peak IV to Peak III area ratio) and about 5% by weight of water.

The clear solution resulting from the exemplified process can be used topically as an antiperspirant product to inhibit or prevent unarm perspiration and odor, or it be used as a manufacturing intermediate in making other antiperspirant and deodorant product formulations.

What is claimed is:

1. A process for making anhydrous compositions containing solubilized, enhanced antiperspirant active, which process comprises the steps of:
   (A) heating an aqueous solution comprising from about 24% to about 55% by weight of a solubilized, non-enhanced, aluminum-containing antiperspirant active at a temperature of from 120° C. to about 200° C. for a period of time of from about 1 minute to about 15 minutes to form a solubilized, enhanced, aluminum-containing antiperspirant active;
   (B) adding a zirconium-containing antiperspirant active to the heated solution to provide the solution with a range of from about 24% to about 60% by weight of the combined solubilized zirconium-containing and aluminum-containing antiperspirant actives;
   (C) adding an anhydrous solvent to the zirconium and aluminum-containing solution at a weight ratio of the anhydrous solvent to the combined zirconium and aluminum-containing antiperspirant actives of from about 1:2 to about 20:1;
   (D) removing water from the anhydrous solvent-containing solution to form an anhydrous composition containing solubilized, enhanced, zirconium-containing and aluminum-containing, antiperspirant active.

2. The process of claim 1 wherein the weight ratio of the anhydrous solvent to the combined zirconium-containing and aluminum-containing antiperspirant active is from about 1:1 to 10:1.

3. The process of claim 1 wherein the weight ratio of the anhydrous solvent to the combined zirconium-containing and aluminum-containing antiperspirant active is from about 2:1 to 4:1.

4. The process of claim 1 wherein the anhydrous solvent is selected from the group consisting of ethylene glycol, polyethylene glycols, dipropylene glycol, sorbitol, diethylene glycol, butylene glycol, hexylene glycol, 1,2-proplyene glycol, 1,3-propylene glycol, glycerine, 1,2-hexanediol, 2-ethyl-1,3-hexane-diol, 1,2,6-hexanetriol, ethanol, tripropylene glycol, propylene glycol methyl ether, isopropyl glyerol ether, dipropylene glycol methyl ether and combinations thereof.

5. The process of claim 1 wherein the anhydrous solvent is selected from the group consisting of propylene glycol, glycerin, 1,2-hexandiol, isopropyl glycerol ether, and combinations thereof.

6. The process of claim 1 wherein the aluminum-containing antiperspirant active of step (A) is selected from the group consisting of aluminum halide, aluminum chlorohydrate, aluminum hydroxyhalides, and combinations thereof.

7. The process of claim 1 wherein the zirconium-containing antiperspirant active is selected from the group consisting of zirconyl oxyhalides, zirconyl hydroxyhalides, and combinations thereof.

8. The process of claim 1 wherein the aqueous solution of step (A) comprises from about 30% to about 50% by weight of the solubilized aluminum-containing antiperspirant active.

9. The process of claim 1 wherein the aqueous solution of step (A) is heated to a temperature of from about 140° C. to about 190° C.

10. The process of claim 1 wherein the heated solution of step (B) comprises from about 30% to about 50% by weight of the combined zirconium-containing and aluminum-containing antiperspirant active, wherein the atomic ratio of zirconium to aluminum is from 1:1 to about 4:1.

11. The process of claim 1 wherein the solubilized, enhanced, aluminum-containing antiperspirant active has a Peak III to Peak IV area ratio of at least about 0.1:1.

12. The process of claim 1 wherein the solubilized, enhanced, aluminum-containing antiperspirant active has a Peak III to Peak IV area ratio of at least about 0.3:1.

13. A process for making anhydrous compositions containing solubilized, enhanced antiperspirant active, which process comprises the steps of:
   (A) heating an aqueous solution comprising from about 24% to about 55% by weight of a solubilized, non-enhanced, aluminum-containing antiperspirant active at a temperature of from 120° C. to about 200° C. for a period of time of from about 1 minute to about 15 minutes to form a solubilized, enhanced, aluminum-containing antiperspirant active;

(B) adding an anhydrous solvent to the aluminum-containing solution at a weight ratio of the anhydrous solvent to the aluminum-containing antiperspirant actives of from about 1:2 to about 20:1; and (C) removing water from the anhydrous solvent-containing solution to form an anhydrous composition containing solubilized, enhanced, aluminum-containing, antiperspirant active.

14. The process of claim 13 wherein the weight ratio of the anhydrous solvent to the aluminum-containing antiperspirant active is from about 1:1 to 10:1.

15. The process of claim 13 wherein the weight ratio of the anhydrous solvent to the aluminum-containing antiperspirant active is from about 2:1 to 4:1.

16. The process of claim 13 wherein the anhydrous solvent is selected from the group consisting of ethylene glycol, polyethylene glycols, dipropylene glycol, sorbitol, diethylene glycol, butylene glycol, hexylene glycol, 1,2-proplyene glycol, 1,3-propylene glycol, glycerine, 1,2-hexanediol, 2-ethyl-1,3-hexanediol, 1,2,6-hexanetriol, ethanol, tripropylene glycol, propylene glycol methyl ether, isopropyl glycerol ether, dipropylene glycol methyl ether and combinations thereof.

17. The process of claim 13 wherein the anhydrous solvent is selected from the group consisting of propylene glycol, glycerin, 1,2-hexandiol, isopropyl glycerol ether, and combinations thereof.

18. The process of claim 13 wherein the aluminum-containing antiperspirant active of step (A) is selected from the group consisting of aluminum halide, aluminum chlorohydrate, aluminum hydroxyhalides, and combinations thereof.

19. The process of claim 13 wherein the aqueous solution of step (A) comprises from about 30% to about 50% by weight of the solubilized aluminum-containing antiperspirant active.

20. The process of claim 13 wherein the aqueous solution of step (A) is heated to a temperature of from about 140° C. to about 190° C.

21. The process of claim 13 wherein the solubilized, enhanced, aluminum-containing antiperspirant active has a Peak III to Peak IV area ratio of at least about 0.1:1.

22. The process of claim 13 wherein the solubilized, enhanced, aluminum-containing antiperspirant active has a Peak III to Peak IV area ratio of at least about 0.3:1.

* * * * *